United States Patent [19]
Tsuchiya et al.

[11] Patent Number: 5,277,674
[45] Date of Patent: Jan. 11, 1994

[54] LEG EXTENSION APPARATUS WITH PIVOTAL FOOT SECTION FOR MEASURING INSTANTANEOUS POWER GENERATED BY A LEG EXTENDING FORCE

[75] Inventors: Kunimasa Tsuchiya; Masao Ito, both of Tokyo, Japan

[73] Assignee: Combi Corporation, Tokyo, Japan

[21] Appl. No.: 821,772

[22] Filed: Jan. 16, 1992

[30] Foreign Application Priority Data

Mar. 30, 1991 [JP] Japan ................................. 3-67320
Mar. 30, 1991 [JP] Japan ................................. 3-67321

[51] Int. Cl.⁵ ...................... A63B 71/00; A63B 23/04; A61B 5/22
[52] U.S. Cl. ............................... 482/8; 482/80; 73/379.06; 73/379.04; 128/779; 128/782
[58] Field of Search ...... 128/774, 779, 782, 25R, 25C, 25B; 482/8, 900, 901, 903, 908, 70–72, 1, 4, 80, 121, 128; 73/379, 865.1, 379.06, 379.04, 862.381, 12.01; 364/413.02, 413.01; 602/23, 62

[56] References Cited

U.S. PATENT DOCUMENTS

| | | |
|---|---|---|
| 3,323,366 | 6/1967 | Lorme et al. |
| 3,387,493 | 6/1968 | Strittmatter |
| 3,734,495 | 5/1973 | Nist et al. |
| 3,752,144 | 8/1973 | Weigle ........................... 73/379 X |
| 4,621,620 | 11/1986 | Anderson ...................... 128/25 R |
| 4,678,182 | 7/1987 | Nakao et al. |
| 4,735,410 | 4/1988 | Nobuta |
| 4,790,528 | 12/1988 | Nakao et al. |
| 4,800,310 | 1/1989 | Nakao et al. |
| 4,817,938 | 4/1989 | Nakao et al. |
| 4,890,495 | 1/1990 | Slane .................................. 73/379 |
| 4,979,733 | 12/1990 | Prud'Hon ...................... 482/116 X |
| 5,035,233 | 7/1991 | Ruf ..................................... 128/25 B |
| 5,131,895 | 7/1992 | Rogers, Jr. ........................... 482/70 |

FOREIGN PATENT DOCUMENTS

| | | |
|---|---|---|
| 0131088 | 1/1985 | European Pat. Off. |
| 0151066 | 8/1985 | European Pat. Off. |
| 0267071 | 5/1988 | European Pat. Off. |
| 0379227 | 7/1990 | European Pat. Off. |
| 0430067 | 6/1991 | European Pat. Off. |
| 8203228 | 3/1984 | Netherlands ...................... 73/379 |
| 1426540 | 9/1988 | U.S.S.R. .......................... 128/774 |

Primary Examiner—Richard J. Apley
Assistant Examiner—John P. Leubecker
Attorney, Agent, or Firm—Sughrue, Mion, Zinn, Macpeak & Seas

[57] ABSTRACT

An apparatus for measuring physical strength by dynamically measuring the instantaneous power of a non-repetitive muscular force as, for example, the force exerted by a leg extension, on the basis of a power theory and, consequently, the instantaneous power generated by a dynamic, nonrepetitive multi-articular movement such as a vertical jump. The power produced by a leg extension is calculated from the maximum speed $V_{max}$ of the foot plate and its output time $T_{max}$. An apparatus for such measurement includes a base frame; a guide section that extends in the same direction as the base frame; a foot section that slides along the guide section so that its sliding angle is variable; a measuring unit that measures sliding conditions of the foot section; a display unit that displays, visually or aurally, various data on the leg extension of the subject; and a processor means for calculating the power generated by the leg extending force.

13 Claims, 8 Drawing Sheets

$C_U$ : CONTINUOUS UP-COUNT   $C_D$ : CONTINUOUS DOWN-COUNT $C_{P1}, C_{P2}$ : PEAK COUNT VALUE

LEG EXTENSION APPARATUS WITH PIVOTAL FOOT SECTION FOR MEASURING INSTANTANEOUS POWER GENERATED BY A LEG EXTENDING FORCE

BACKGROUND OF THE INVENTION

This invention relates to an apparatus for and method of measuring the physical strength of a person. More particularly, it is directed to an apparatus for and method of dynamically measuring the instantaneous power of a nonrepetitive muscular force as, for example, the force of a leg extending motion, based on a power theory. Specifically, the apparatus and method involve measuring the instantaneous power of a dynamic, nonrepetitive multi-articular motion as, for example, a vertical jump.

Conventional physical strength tests, such as vertical jump tests, reciprocal jump tests, and dorsal muscle tests, have had the following problems:

(1) It is often difficult to synthesize separate test results sized for evaluation, since various functions are evaluated separately.

(2) Evaluation standards are ambiguous. For example, the evaluation standard of a vertical jump is the height to which one can jump; however, this is merely an indirect index of physical strength.

(3) There is no standardized scientific support.

(4) Unusual movements may be involved, the loads involved are large, and injuries are liable to occur.

Presently, there is growing interest in physical conditioning. Thus, a method of and apparatus for easily, safely and accurately measuring physical strength is needed. In response, a study on unified indices of physical strength based on a power theory is underway.

According to the power theory, physical strength is measured as the capacity of energy (an integrated value of the power) or as an index. Methods for the generation of power can be classified according to energy developing mechanisms within a living body. For each method of power generation, an upper limit of power is measured and used as an index of physical strength for the corresponding energy generating mechanism.

Specifically, the mechanisms are classified as follows:
(a) Oxygen-present energy mechanism
  Duration: Infinite
  Evaluation of upper limit power: Power available at 75% of the maximum heart rate, etc.
  Main factor for energy generation: Oxygen
(b) Lactic acid-type anaerobic energy mechanism
  Duration: About 30 seconds
  Evaluation of upper limit power: Average power, critical power, etc.
  Main factor for energy generation: Glycogen
(c) Non-lactic acid-type anaerobic energy mechanism
  Duration: About 7 seconds
  Evaluation of upper limit power: The optimum value determined by speed and developing force of the peak power around 5 to 6 seconds.
  Main factor for energy generation: ATP-CP type chemical energy.

With respect to energy mechanisms (a) and (c), a measuring apparatus using a bicycle ergometer has been practiced by the applicant (Japanese Patent Examined Publication No. 42694/1989). "AEROBIKE" and "POWERMAX" are also known apparatuses developed from the above art. (Both "AEROBIKE" and "POWERMAX" are registered and pending trademarks of Combi Corporation; the former is Japanese Trademark Registration No. 1840771, and the latter is Japanese Trademark Publication No. 61-42348.) As for energy mechanism (b), the Wingate test is an example.

Power measurement by means of a bicycle ergometer has the advantage of rhythmic and efficient pedaling motion which lessens the chance of injury.

The instantaneous power of a dynamic, nonrepetitive muscular force in continuous muscular exercise of one's legs or other similar multi-articular exercise can be advantageous in every day life as, for example, when one must hastily avoid an obstacle. One apparatus for measuring the instantaneous power of a nonrepetitive muscular motion of legs is disclosed in Japanese Utility Model Unexamined Publication No. 18103/1988. In this publication, the leg extending power is transmitted to an hydraulic or pneumatic cylinder, and the physical strength of a subject is measured according to data from the cylinder.

In the above leg extending, power measuring apparatus, the adjustment of the cylinder and the like is very difficult, and the variation of the load in accordance with the speed makes it difficult to accurately measure instantaneous power. Further, with a hydraulic cylinder, the response time of the hydraulic pressure is so slow as to make measurement accuracy unreliable.

Instantaneous power generated by a leg extending force is conventionally calculated from the amount of work done on a brake load. The foot plate, having to receive the force generated when the user or subject kicks it with his full power within a very short time (about 0.3 seconds), is heavy and rigid in structure. Kinetic and inertial energy, as absorbed by the foot plate and the rotating system of a brake, are not taken into consideration in such calculations. Therefore, it is difficult to accurately measure the instantaneous power generated by leg extension.

SUMMARY OF THE INVENTION

The present invention has been made in view of the above considerations and is directed to the accurate measurement of instantaneous power by the power theory, whereby unstable factors involved in the measuring system are eliminated to the extent possible.

An object of the invention is to provide an apparatus for and method of measuring the instantaneous power generated by a leg extending force, in which a powder brake is used to reduce the influence of inertia on the power measurement. The present invention, as compared with conventional power measurements based on non-lactic acid-type anaerobic energy mechanisms, attempts to minimize the time required to push a foot plate, so that stress on the user or subject involved in the measurement is attendantly reduced.

Another object is to provide a method for measuring an instantaneous power generated by a leg extending force, in which a device used to produce a load is of a constant torque type rather than a hydraulic or dynamo type whereby the load is varied by the foot-pressing speed. In view of the fact that the response time of the load to the powder brake is approximately 200 ms, it is difficult to change the load during a measurement whose duration is approximately 0.3 seconds. Thus, a constant-torque system is proposed to increase measurement accuracy. The present invention employs this system and attempts to eliminate load variations during measurement, thereby stabilizing the measurement.

A further object is to provide a method of and apparatus for measuring the instantaneous power generated by a leg extending force, in which the angle of the foot plate is automatically varied in accordance with the amount of leg extension. In conventional apparatus, the angle of the foot plate is fixed, making the foot-pressing force unstable because of changes in the angle of inclination of the subject's foot during leg extension.

Figure 1:
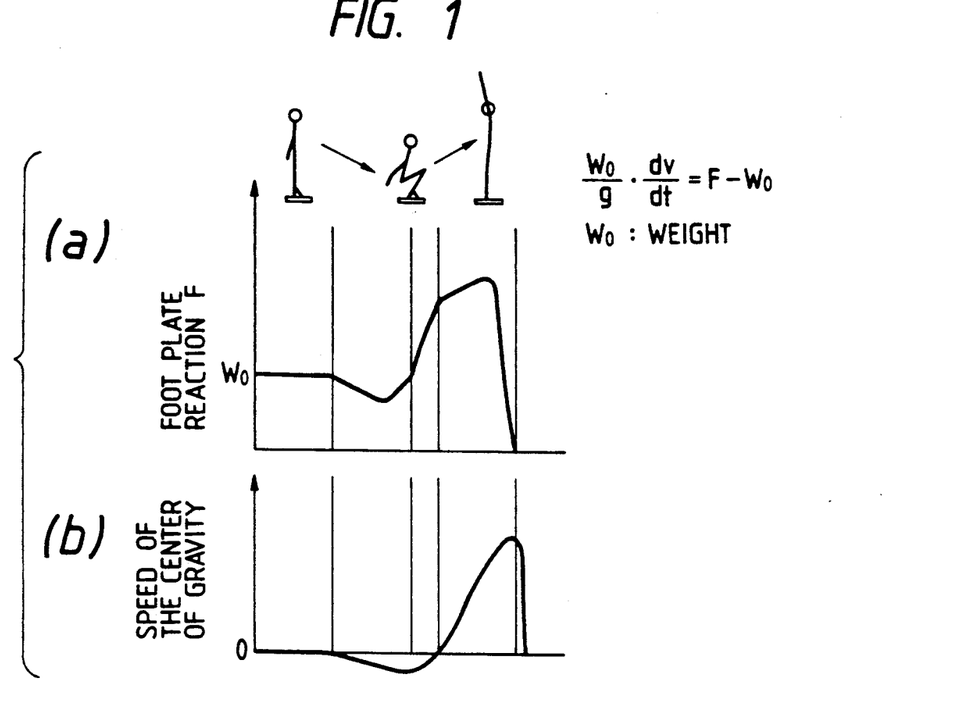
FIGS. 1A and 1B are diagrams showing the relationship between a foot plate reaction obtained from a vertical jump and the center of gravity of a human being.
Figure 2:
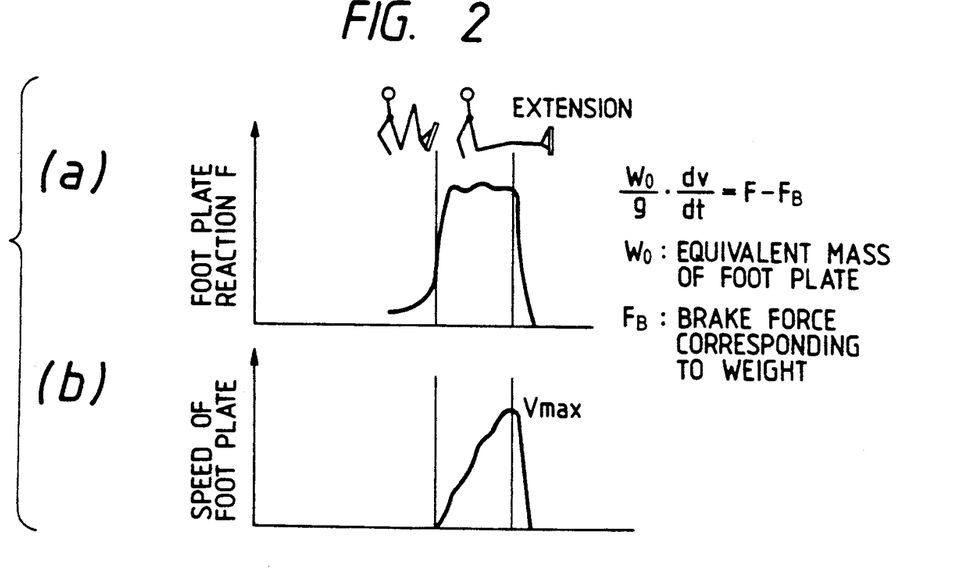
FIGS. 2A and 2B are diagrams showing the relationship between a foot plate reaction obtained from a vertical jump and a foot plate speed.

To achieve the above objects, attention is paid to the fact that the relationship between the foot plate reaction produced by a vertical jump and the speed of the center of gravity of a subject, as shown in FIGS. 1 (a) and (b), is directly related to the leg extension as seen in FIGS. 2 (a) and (b). Further, it can be seen from kinetic equations that the powder brake load is equivalent to the gravitational weight applied by the lower extremities of a subject during a vertical jump, and that the inertial mass, $W_0/g$, is equivalent to the subject's upper extremity mass as an inertial force during the vertical jump. More particularly, a leg extension measuring apparatus involves motions of the lower extremities which are similar to a vertical jump, such that it is sufficient to use the inertial mass of a horizontally moving upper extremity. For example, a person who weighs 65 kg selects, as an equivalent mass of 1 $W_0/g$ of the foot plate, a weight range of 40 to 50 kg into which his upper extremity weight of 46 kg falls (it is said that approximately 70% of the total weight of a person is attributable to upper extremity mass), and measures his leg extending power analogous to a vertical jump by giving the foot plate an equivalent mass corresponding to the upper extremity mass. In other words, the foot plate equivalent mass is selected to be equivalent to the upper extremity mass of a person so as to allow the measurement of a leg extending power in a manner analogous to a vertical jump.

Use of a power sensor mounted on the foot plate is structurally complicated and makes the operation cumbersome. Furthermore, the provision of braking means to prevent impact on one's feet due to the heavy structure of the foot plate may lead to errors in the measurement of the instantaneous power generated by a leg extending motion. In addition, the likelihood exists that the foot plate will pull out the legs due to inertia, thus making the structure dangerous. The present invention attempts to overcome these problems.

To achieve the above objects, the present invention provides a method of and apparatus for measuring an instantaneous power generated by a leg extending force. The method includes calculating a maximum speed $V_{max}$ of the foot plate and its output time $T_{max}$ by adding the work corresponding to an equivalent energy of inertia absorbed by a rotary drive system consisting of a powder brake, an intermediate shaft, and a rope drum shaft and the work corresponding to the actual kinetic energy as obtained by the foot plate to the work applied to the powder brake. Thus, the power produced by leg extension can be calculated from the maximum speed $V_{max}$ of the foot plate and its output time $T_{max}$.

Further, to achieve the above objects, the invention provides an apparatus with a base frame in which two long members are mounted parallel to each other, a box disposed in the rear of the base frame, and a drive unit installed inside the box. A seat is disposed above the drive unit and thus on the upper surface of the box. A guide section extends in the same direction as the base frame between the upper front surface of the box and a vertical plate standing at the front end of the base frame, with the upper front surface of the box serving as the base end. A foot section slides back and forth along the guide section so that its sliding angle is variable. A measuring unit measures sliding conditions of the foot section. A display section displays, visually or aurally, various data on the subject's leg extension as measured by the measuring unit. The subject inputs predetermined data required in carrying out a measurement through an input section.

The invention, adopting the above method, can measure an instantaneous power by a very quick, full-power kick to the foot plate, involving a natural motion and imposing less physical burden on the subject. Thus, the invention measures the leg extending power of a subject in an extremely simple manner and with a high degree of accuracy.

The above full-power kicking allows the measurement of an instantaneous power of a leg extending force generated during a dynamic, nonrepetitive multi-articular exercise such as a vertical jump.

BRIEF DESCRIPTION OF THE DRAWINGS

FIG. 10 (a) and (b) are sectional views showing one example of the powder brake.

DETAILED DESCRIPTION OF THE PREFERRED EMBODIMENT

In the figures, an apparatus 1 measures an instantaneous power generated by a leg extending force, said apparatus being applied to the present method for measuring an instantaneous power generated by a leg extending force. In apparatus 1, a base frame 2 includes two long members 2a (made of metallic square bars in this embodiment) mounted parallel to each other. A box 3 is disposed in the rear of the base frame 2. A drive unit 4 is installed inside the box 3. A seat 5, disposed above the drive unit 4 and thus on the upper surface of the box 3, seats a subject M. A guide section 6 extends in the same direction as the base frame between the upper front surface of the box 3 and a vertical plate 2b that stands at the front end of the base frame 2, with the upper front surface of the box serving as the base end. A foot section 7 slides back and forth along the guide section 6 so that its sliding angle is variable. A measuring unit 8 measures sliding conditions of the foot section 7. A display section 9 displays, visually or aurally, various data on the leg extension of the subject M measured by the measuring unit 8. The subject M inputs predetermined data required in carrying out a measurement to an input section 10.

The two long members 2a forming the base frame 2 are arranged so as to extend parallel to each other while interposing a predetermined distance therebetween. On the rear end of each long member 2a is a vertically adjustable caster 2c. Additionally, a total of four fixed adjusters 2d are arranged such that two are located at both sides near the lower front surface of the box 3 and two are located at both sides under the vertical plate 2b that stands at the front end of the base frame 2. These adjusters 2d serve to horizontally hold and stably fix the base frame 2.

The box 3 is formed by placing a plate 3b so as to be surrounded by four pillars 3a that are mounted upright in the rear side of the base frame 2.

Figure 3:
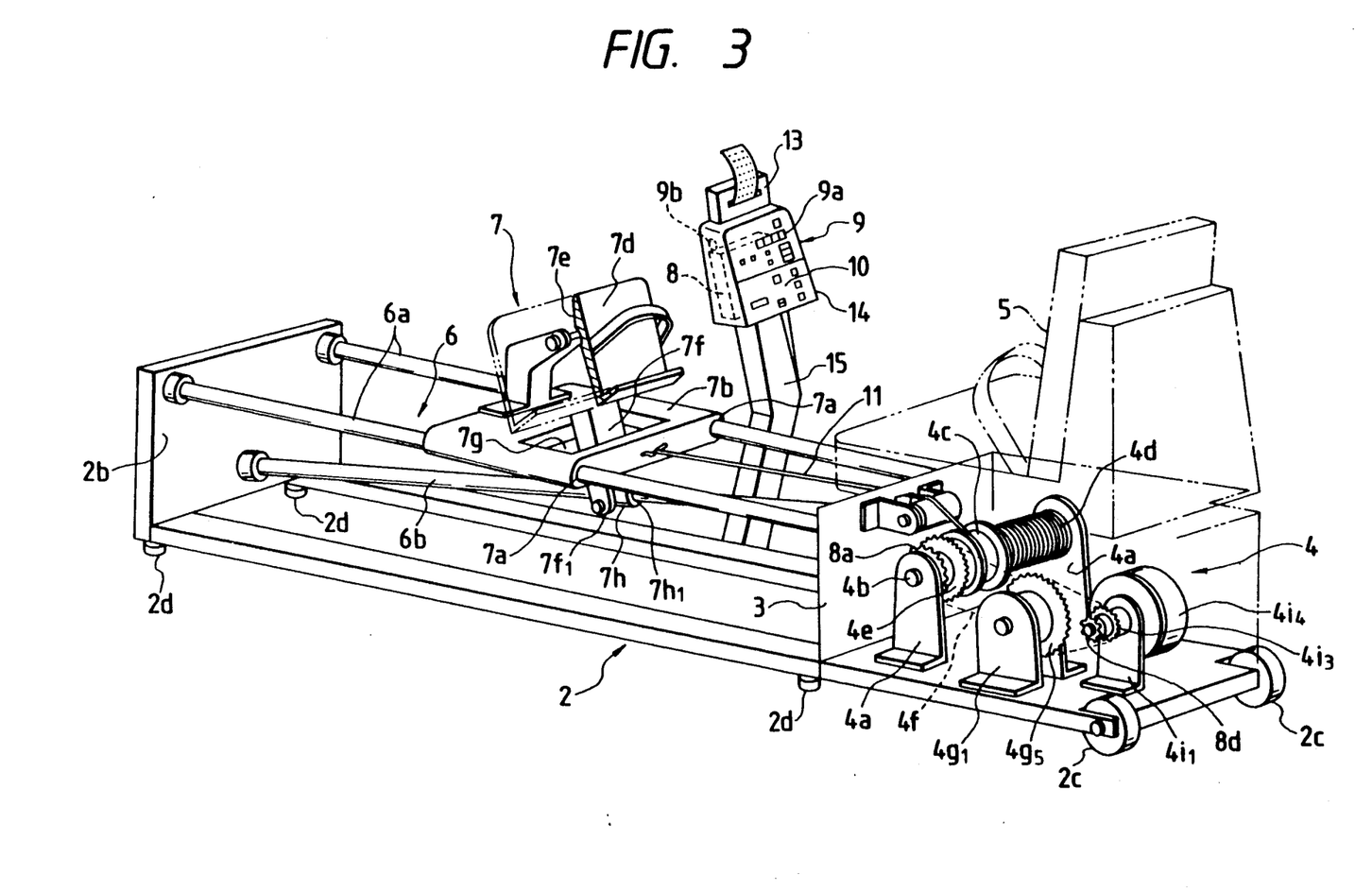
FIG. 3 is a perspective view of the general construction of an apparatus according to the present invention.
Figure 5:
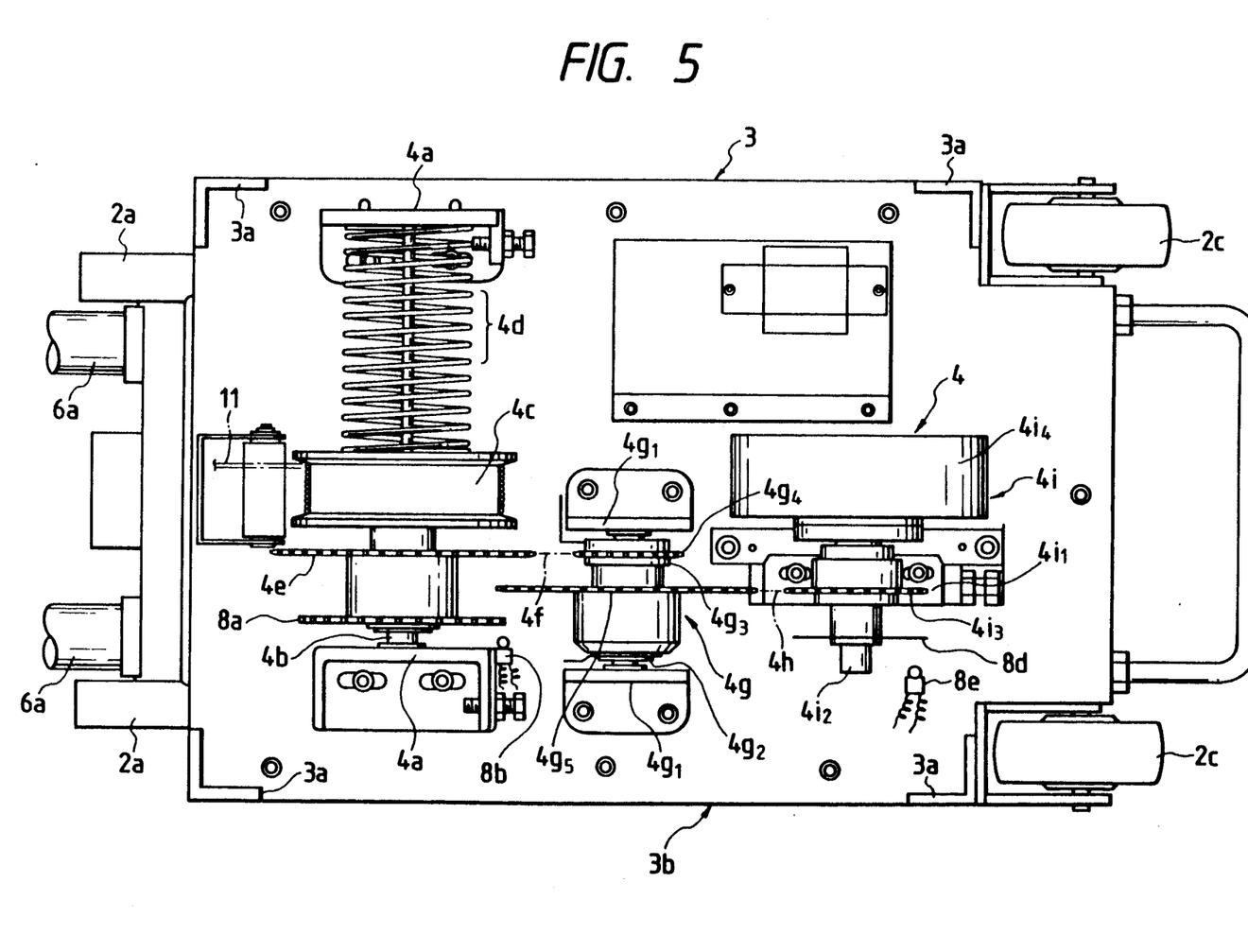
FIG. 5 is a plan view showing the main portion of a drive unit of the apparatus.
Figure 6:
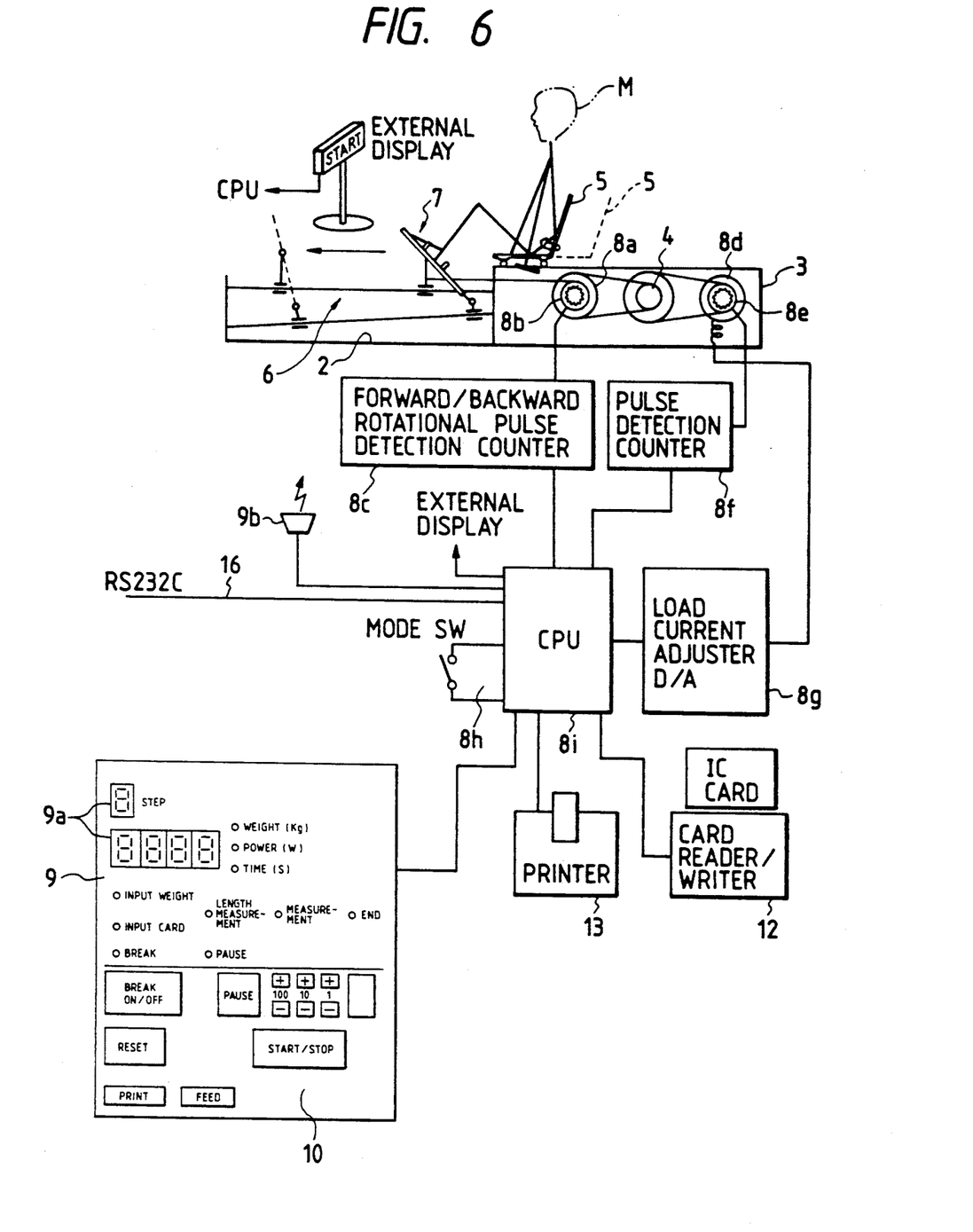
FIG. 6 is a block diagram showing the overall apparatus.

The drive unit 4 arranged within the box 3 includes a rope drum 4c around which a rope 11 (described later) is wound, the rope drum 4c being mounted on a rotating shaft 4b supported by brackets 4a that stand upright at both sides of and toward the front end of the box 3. A return spring 4d (formed from a cylindrical spring as shown in FIGS. 3 and 5) is juxtaposed with the rope drum 4c and a first sprocket 4e is disposed at one side of the rope drum 4c.

An intermediate shaft mechanism 4g is rotated unidirectionally through a chain 4f wound around the first sprocket 4e. The intermediate shaft mechanism 4g includes a rotating shaft 4g2 that is supported by both brackets 4g1 standing upright substantially in the middle of the interior of the box 3, a free wheel sprocket 4g4 containing a free wheel 4g3 mounted on the rotating shaft 4g2 and around which the chain 4f is wound, and a third sprocket 4g5 similarly fixed on the rotating shaft 4g2.

A powder brake mechanism 4i is rotated unidirectionally through a chain 4h wound around the third sprocket 4g5. The powder brake mechanism 4i includes a bracket 4i1 standing upright in the rear of the box 3, a rotating shaft 4i2 inserted into the bracket 4i1, a fourth sprocket 4i3 that is fixed on the rotating shaft 4i2 and rotated unidirectionally by the chain 4h, and a powder brake 4i4 that is rotated around the rotating shaft 4i2.

Figure 10A:
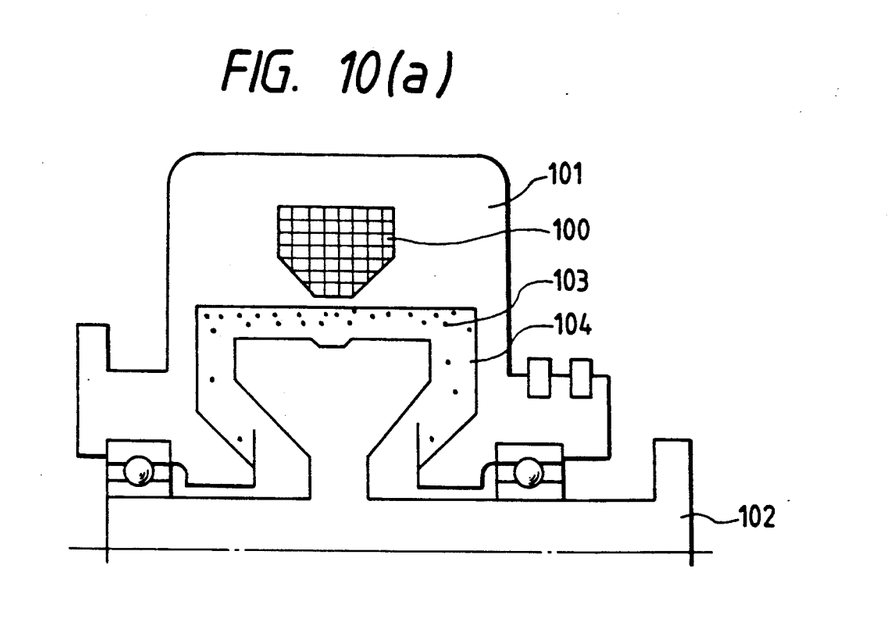
Figure 10B:
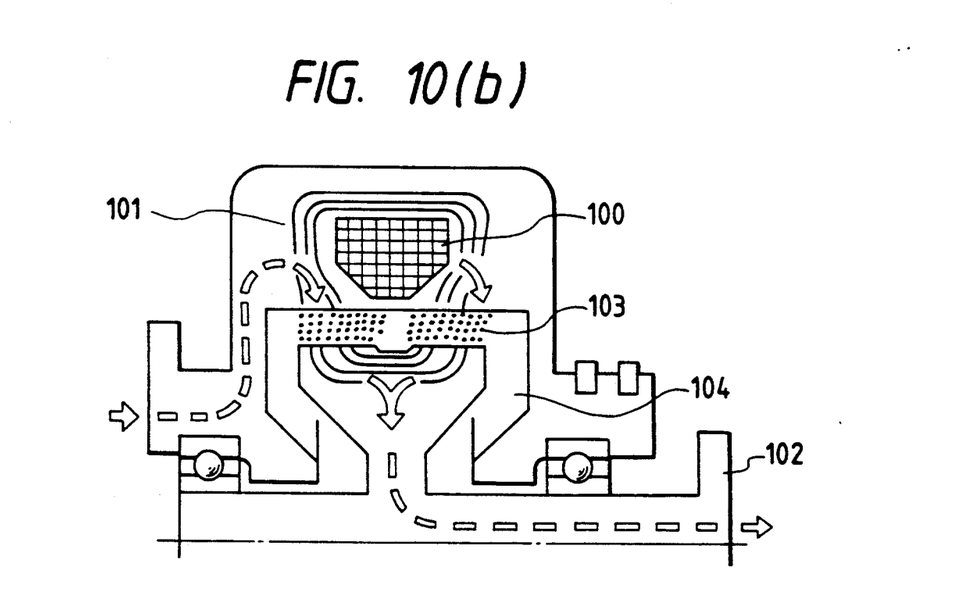

FIG. 10 (a) and (b) are sectional views showing one example of the powder brake. As shown in FIG. 10 (a), when a current does not flow to an excitation coil 100, a drive member 101 is in a release condition so as not to transmit the torque to a driven member 102. In this condition, powder 103 (for example, magnetic powder) adheres to the outer periphery of a powder gap 104 formed between the driven member 102 and drive member 101. One of the drive and driven members is secured.

On the other hand, as shown in FIG. 10 (b), when the current flows to the excitation coil 100, the powder 103 is magnetized to form the solid state in the gap so that the torque is transmitted to the driven member 102. Solid lines designate a magnetic flux, and dot lines designate a torque transmitting path.

The seat 5 for seating the subject M is disposed above the drive unit 4 on the upper surface of the box 3 and is constructed so that it can be adjusted to an appropriate position by horizontally sliding parallel adjust guide shafts 5a by a predetermined distance while inserting them into shaft receiving members 5b. The adjust guide shafts 5a are arranged at both sides under the lower surface of the seat 5, and the shaft receiving members 5b are formed so as to protrude from the upper surface of the box 3.

The guide section 6, extending in the same direction as the base frame from the upper front surface of the box 3, includes right and left upper guide shafts 6a, each of which extends horizontally between the upper front surface of the box 3 and the vertical plate 2b standing at the front end of the base frame 2. A lower guide shaft 6b runs along the guide shafts 6a midway therebetween and inclined so as to be lower at its front end.

The foot section 7, which slides forward and backward along the guide section 6, includes a slider 7b that slides horizontally by inserting the upper guide shafts 6a into its right and left insertion holes 7a (one end of the rope 11 of the rope drum 4c is connected to the slider 7b at the center of its rear end). A foot plate 7e has a back surface that is rotatably hinged by a bracket provided upright at the front of the slider 7b and which has a foot receiving member 7d on its upper surface in which to place both feet of the subject M. The angle of the foot receiving member 7d of the foot plate 7e that moves forward and backward changes with leg extension of the subject M. This angle adjustment is implemented by sliding the foot plate 7 along the lower guide shaft 6b while inserting the lower guide shaft 6b into an insertion hole 7h1 of an oscillatably attached seal boss 7h. The foot plate 7e is slidably mounted on the lower guide shaft 6b through a support member 7f which extends downwardly through an opening 7g formed around the center of the slider 7b, and which is attached to the seal boss 7h by screws through its fork portion 7f1.

The measuring unit 8 that measures sliding conditions of the foot section 7 includes a drum shaft encoder 8a that is secured to the first sprocket 4e of the rope drum 4c. A forward/backward rotational pulse detection counter 8c of the rope drum 4c has a photosensor 8b for detecting the number of revolutions of the drum shaft encoder 8a. A load shaft encoder 8d is secured to the rotating shaft 4i2 of the powder brake mechanism 4i. A load shaft rotational pulse detection counter 8f detects the rotation of the powder brake 4i4, the counter 8f having a photosensor 8e for detecting the rotation of the load shaft encoder 8d. A load current adjuster 8g adjusts the current of the powder brake 4i4. A processor 8i (hereinafter, referred to as the "microcomputer") calculates the leg extending force at the time the subject M kicks the foot plate 7e repetitively, for an appropriate number of times, from signals such as pulse signals sent from the pulse detection counters 8c, 8f, a mode signal selected by a mode selector switch 8h, and a data signal inputted from the input section 10 (described later).

The measuring unit 8 has an IC card reader/writer 12 at an appropriate location other than the drum shaft encoder 8a, a photosensor 8b that detects the number of revolutions of the drum shaft encoder 8a, a load shaft encoder 8d, and a photosensor 8e that detects the rotation of the load shaft encoder 8d. The card reader/writer 12 is installed inside a cabinet 14 that has a printer 13 for recording the measurement results. The IC card reader/writer 12 and the printer 13 are provided to facilitate management of input weight data and output power data of the subject M by a higher level computer.

The cabinet 14 is installed onto an arm 15 that releaseably stands on a lateral side of the base frame 2a at such a position as to allow the subject M seated in the seat 5 to operate it easily.

The display section 9, which displays, visually or aurally, predetermined values measured by the measuring unit 8, such as a step count, a weight of the subject M (kg), a power (W), and a required time (S), includes LED display unit 9a and a buzzer 9b. The LED display unit 9a is located on an upper front portion of the cabinet 14 into which the measuring unit 8 and buzzer 9b are positioned.

The input section 10 for inputting various data such as a weight of the subject to the microcomputer 8i includes keys 10b or the like that are similarly arranged on a lower front portion of the cabinet 14.

An output of the microcomputer 8i is applied to the powder brake 4i4 through the load current adjuster 8g, so that the forward sliding of the foot plate 7e brought about by the subject M kicking the foot plate 7e is braked. A so-called "automatic braking mechanism" is used. The mechanism is made up of a simple brake utilizing the measurement of length of the legs of the subject M and which can detect $V_{max}$ of the foot plate 7e on a realtime basis. The position at which the foot plate 7e is braked is preset to a maximum length measured to be equal to the distance a subject M extends his legs under a natural condition, so that inertial impact produced at the end of kicking the foot plate 7e can be prevented, and stable measurement can thereby be implemented.

Data in the microcomputer 8i is intercommunicated to a host computer (not shown) through an interface circuit 16, so that the measurement results can also be managed by external devices.

The leg extending force of the subject M can be accurately calculated by the microcomputer 8i as follows. First, a leg extending force produced by the subject M kicking the foot plate 7e is transmitted to the rope drum 4c through the rope 11. A rope drum 4c rotational count signal is input to the microcomputer 8i through the forward/backward rotational pulse detection counter 8c while detecting, by the photosensor 8b, the number of revolutions of the drum shaft encoder 8a which rotates as the rope drum 4c rotates. The rotation of the rope drum 4c is transmitted to the final destination, i.e., the powder brake 4i4, through the first sprocket 4e and the intermediate shaft mechanism 4g. The rotation of the load shaft encoder 8d secured to the rotating shaft 4i2 of the powder brake 4i4 is detected by the photosensor 8e. Finally, the detected load shaft rotation signal is applied to the microcomputer 8i through the load shaft rotation pulse detection counter 8f.

For the above calculation, the present invention uses the equivalent mass of the rotary systems such as the rotating shaft 4b of the rope drum 4c, the rotating shaft 4g2 forming the intermediate shaft mechanism 4g, and the powder brake 4i4 to improve measurement accuracy.

Assuming a moment of inertia J at the rope drum shaft (including the intermediate shaft and the powder brake), the following relationship is established:

$$J \cdot \frac{2\pi}{60} \cdot \frac{dN}{dt} = J \cdot \frac{dw}{dt} = T; \quad (1)$$

$$\omega = \frac{v}{r}; J \cdot \frac{1}{r} \cdot \frac{dv}{dt} = r \cdot F_S$$

$$F_S = J/r^2 \cdot \frac{dv}{dt} \quad (2)$$

$$M_J = J/r^2 \quad (3)$$

where
T: Brake torque applied to drum shaft [kgm]
$\omega$: Angular velocity of drum [rad/s]
N: Number of revolutions of drum [rpm]
v: Rope speed [m/s]
$F_s$: Tensile force applied to rope [kgf]

By adding the actual mass of the foot plate 7e to the equivalent mass of the rotary system thus calculated, the kinetic equation of the leg extending force of a subject M is obtained in the following manner.

Assuming a mass $M_F$ of the foot plate itself, the total mass $M_0$ becomes $$M_0 = M_F + M_J \quad (4)$$

Hence, $$M_0 \frac{dv}{dt} = F - F_B \quad (5)$$

where
F: Leg extending force produced by a person [N]
$F_B$: Brake force produced by powder brake [N]

Expressing $M_0$ by the load $W_0$ [kgf] in the system of gravitational units, $$\frac{W_o}{g} \cdot \frac{dv}{dt} = F - F_B \quad (6)$$

where
$W_0$: [kgf]
$F, F_B$: [kgf]
g: 9.8 [m/s$^2$]

Once the kinetic equation for leg extension has been obtained, the rotation of the drum shaft encoder 8a and of the load shaft encoder 8d allows the leg extending force to be inferred from the maximum foot plate speed $V_{max}$ and its output time $T_{max}$; i.e., the force produced by a leg extension of the subject M is first calculated. Next, the work equivalent to the energy of inertia absorbed by the rotary system (consisting of the powder brake 4i4, the rotating shaft 4g2 of the intermediate shaft mechanism 4g, and the rotating shaft 4b of the rope drum 4c) and the work equivalent to the kinetic energy obtained by the foot plate 7e are added to the work done to the powder brake 4i4. The added value is defined as a new type of leg extending force unique to the invention, and an average leg extending force of the subject M is obtained by a predetermined calculation.

When the legs are extended horizontally from an origin, (assuming that the maximum rope speed V is $V_{max}$ and the time during which $V_{max}$ has been produced, or its output time, is $\tau_{max}$), the maximum leg stroke $l_{max}$ is as follows.

$$l_{max} = \int_0^{\tau_{max}} v dt \; [m] \quad (7)$$

If the change in the rope speed V from 0 to $V_{max}$ is linearly approximated, $$l_{max} \sim \tfrac{1}{2} \times \tau_{max} \times V_{max} \quad (8)$$

When a person kicks the foot plate that weighs $W_0$, assuming that the obtained velocity is v, the kinetic energy produced by the foot plate is as follows.

Kinetic energy obtained by $W_0$ is:

$$\frac{1}{2} M_o \cdot v^2 = \frac{1}{2} \cdot \frac{W_o}{g} \cdot v^2$$

When this is differentiated by time, $$\frac{d}{dt}\left(\frac{1}{2} \cdot \frac{W_o}{g} \cdot v^2\right) = \frac{1}{2} \cdot \frac{W_o}{g} \cdot 2v \cdot \frac{dv}{dt} = \frac{W_o}{g} \cdot v \frac{dv}{dt} \quad (9)$$

Using equation (6), if $F - F_B = \Delta F$, $$\frac{d}{dt}\left(\frac{1}{2} \cdot \frac{W_o}{g} \cdot v^2\right) = \Delta F \cdot V = \Delta F \cdot \frac{dx}{dt} \quad (10)$$

$$d\left(\frac{1}{2} \cdot \frac{W_o}{g} \cdot v^2\right) = \Delta F \cdot dx \quad (11)$$

where x is the distance [m] the rope is moved.

Therefore, the kinetic energy obtained by the foot plate up to the moment the rope speed V has reached $V_{max}$ is $$\int_0^{V_{max}} d\left(\frac{1}{2} \cdot \frac{W_o}{g} \cdot v^2\right) = \int_0^{V_{max}} \Delta F \cdot dx = \quad (12)$$

$$\int_0^{V_{max}} \Delta F \cdot dx - \int_0^{V_{max}} F_B \cdot dx$$

$$\frac{1}{2} \cdot \frac{W_o}{g} \cdot v^2_{Vmax} = \int_0^{V_{max}} \Delta F \cdot dx - \int_0^{V_{max}} F_B \cdot dx; \quad (13)$$

$$\int_0^{V_{max}} \Delta F \cdot dx = \frac{1}{2} \cdot \frac{W_o}{g} \cdot V^2_{max} + l_{max} \cdot F_B$$

The left side represents the total work done by the person, while the right side represents the sum of the work converted into the kinetic energy and the work done to the brake.

Substituting from equation (7), $l_{max}$ is $$\int_0^{V_{max}} F \cdot dx = \frac{1}{2} \cdot \frac{W_o}{g} \cdot V^2_{max} + \frac{1}{2} \tau_{max} \cdot V_{max} \cdot F_B \quad (14)$$

Figure 8:
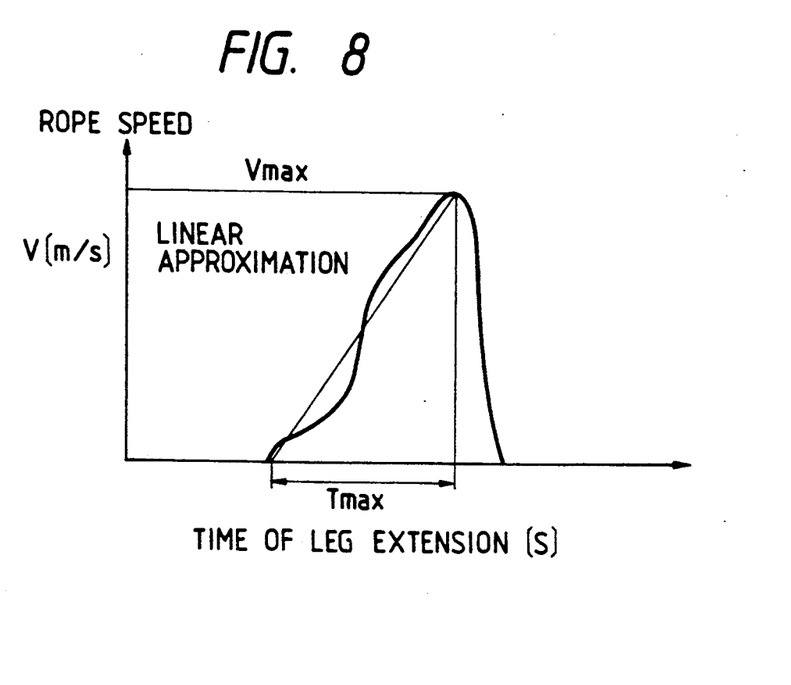
FIG. 8 is a graph for calculating an average leg extending power.

An average power $\bar{P}$ can be calculated as follows.

$$\bar{P} = \frac{1}{\tau_{max}} \int_0^{\tau_{max}} Pdt \, [w] = \frac{1}{\tau_{max}} \quad (15)$$

(Total work performed by the person by a leg extension)

$$= \frac{g}{\tau_{max}} \int_0^{\tau_{max}} Pdt \, [w]$$

$$\frac{g}{\tau_{max}}\left(\frac{1}{2} \cdot \frac{W_o}{g} \cdot V^2_{max} + \frac{1}{2} \tau_{max} \cdot V_{max} \cdot F_B\right) \quad (16)$$

(g serves to convert the unit [kgf] of F to [N])
Hence, $$\bar{P} = \frac{W_o V^2_{max}}{2 \tau_{max}} + \frac{g \cdot V_{max} \cdot F_B}{2} \, [w] \quad (17)$$

Thus, the average leg extending force P can be calculated by measuring $\tau_{max}$ and $V_{max}$.

Assuming that the distance the rope is moved per pulse of the encoder equals $\Delta x_1$ and that the pulse cycle is $\Delta T_1$, then the moving speed of the rope measurable by the load shaft encoder becomes $$V_1 = \frac{\Delta x_1}{\Delta T_1} \quad (18)$$

It is assumed that the distance moved of the rope 11 per rotational pulse of the drum shaft encoder 8a equals $\Delta x$.

Figure 9:
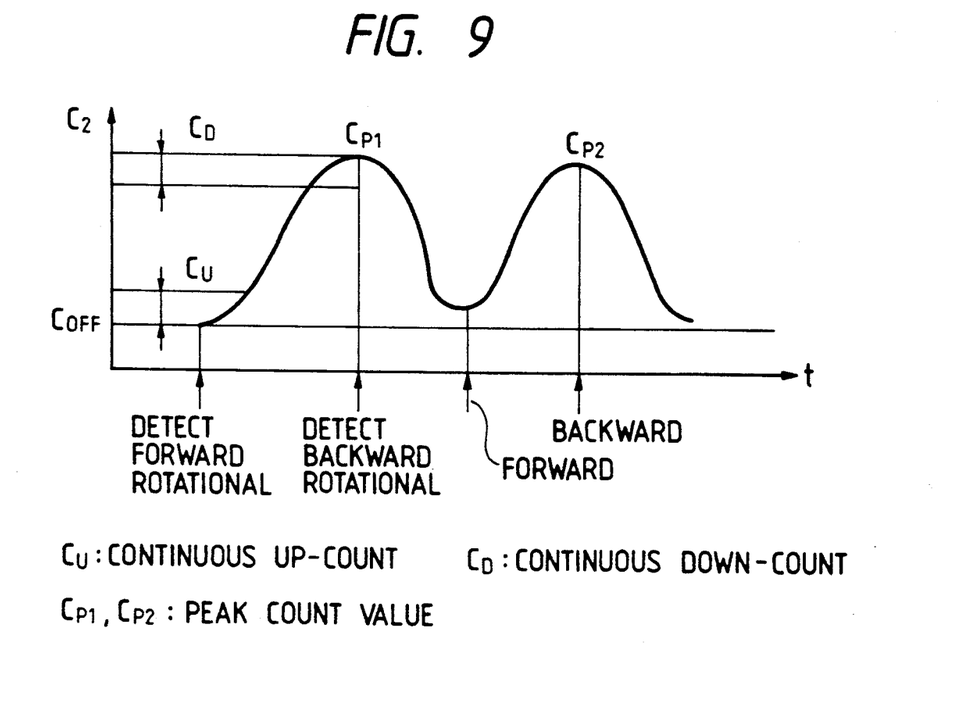
FIG. 9 is a graph showing lengths Lp measured by a drum shaft encoder pulse.

Further, while detecting a forward/backward rotational pulse by the forward/backward rotational pulse detection counter 8c (a two-phase counter), assuming that the drum shaft encoder 8a count is $C_2$ and that the distance the foot plate 7e is moved from the origin is Lp, the offset of $C_2$ becomes $C_{OFF}$ (errors in the foot plate 7e returning to the origin are taken into account). To measure Lp, the subject M must extend his legs twice, lightly, so as to cause the counter to count a value $C_2$. To prevent the occurrence of errors attributable to irregularly shaken feet, the counting is carried out under two conditions: an up-count $C_U$ and a down-count $C_D$ with a certain hysteresis.

$$l = \frac{l_{p1} + l_{p2}}{2} \, [m]; \quad (19)$$

$$l_{p1} = \Delta x_{i2} (C_{p1} - C_{OFF});$$

$$l_{p2} = \Delta x_2 \cdot (C_{p2} - C_{OFF})$$

Here, the error processing is performed when the difference between the two counts is too large as, for example, when $|l_{p1} - l_{p2}| < l_p$.

In calculating the above value, the weight of the subject M is selected as a load to determine the braking value to be set to the powder brake 4i4 in the present method for measuring an instantaneous power generated by a leg extending force, while taking into consideration the fact that the reaction from a vertical jump is exerted by the center of gravity of the weight, as is inferred from the kinetic equation of the vertical jump.

A method for measuring an instantaneous power generated by a leg extending force of the present invention will be described next with reference to the aforesaid apparatus.

Figure 4:
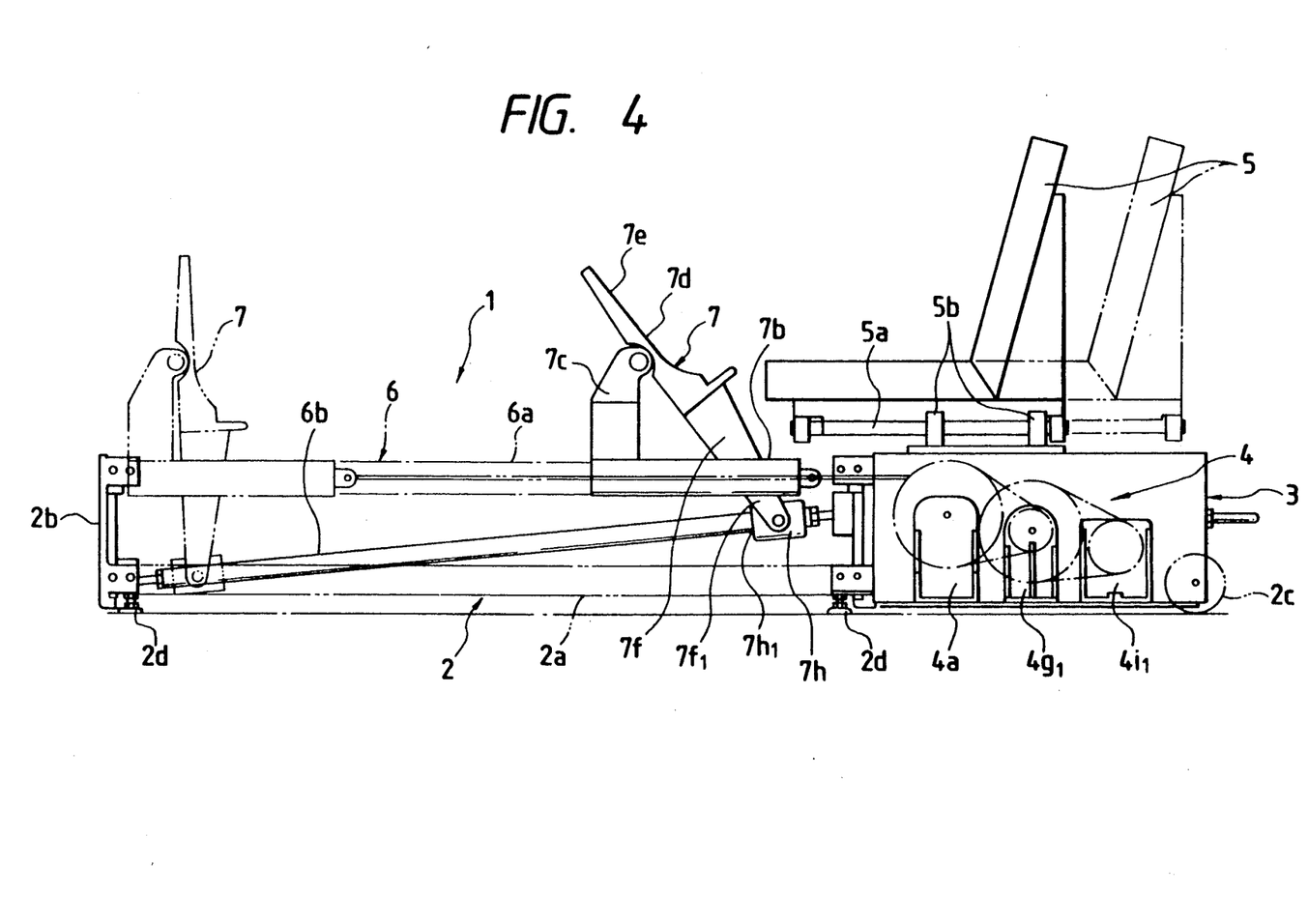
FIG. 4 is a diagram showing the general construction of the apparatus viewed from a side thereof.

The operation of the apparatus 1 for measuring an instantaneous power by a leg extending force is performed as the subject M seated in the seat 5 strongly kicks the foot plate 7e frontward. The foot plate 7e kicked frontward by the subject M is guided by the lower guide shaft 6b which is gradually inclined as the foot plate 7e moves forward along the lower end of the support member 7f. Support member 7f is hinged so as to allow for oscillatory motion with respect to the slider 7b and extends downwardly through the opening 7g of the slider 7b. Thus, the angle formed by the legs of the subject M as they are extended forward and, thus, the angle of the foot plate 7e, change in accordance with the change of the angle of position of the subject M, i.e., from a forwardly inclined position with his legs bent to a substantially vertical position as his legs are extended, as depicted by the solid line and the broken line in FIG. 4. Therefore, the leg extension of the subject M can be measured by causing the subject M to fully extend his legs naturally.

Further, the foot plate 7e kicked by the subject M causes the rope 11 connected at the center of the rear side of the foot plate 7e to be pulled strongly as the foot plate 7e moves forward. As a result, the rope drum 4c having the rope 11 wound therearound rotates, resisting the return spring 4d. This rotation is inputted to the microcomputer 8i through the drum shaft encoder 8a, the photosensor 8b, and the forward/backward rotational pulse detection counter 8c which are equipped at one side of the rotating shaft 4b.

The rotation of the rope drum 4c is transmitted to the powder brake 4i4 through the first sprocket 4e, the chain 4f, the free wheel 4g3, the free wheel sprocket 4g4, the third sprocket 4g5, the chain 4h, and the fourth sprocket 4i3. The rotation of the powder brake 4i4 is inputted to the microcomputer 8i through the load shaft encoder 8d, the photosensor 8e, and the pulse detection counter 8f which are equipped at one side of the rotating shaft 4i2.

As the foot plate 7e kicked by the subject M reaches the position at which leg extension is to be measured, the powder brake 4i4 intervenes so that the subject's feet are not pulled by the weight of the foot plate 7e. Accordingly, the subject M bends his legs to return the foot plate 7e to the original position. The foot plate 7e returns very smoothly because the resilient force of the return spring 4d juxtaposed with the rope drum 4c acts in the forward direction, causing the rope 11 to be wound around the rope drum 4c tightly.

Figure 7:
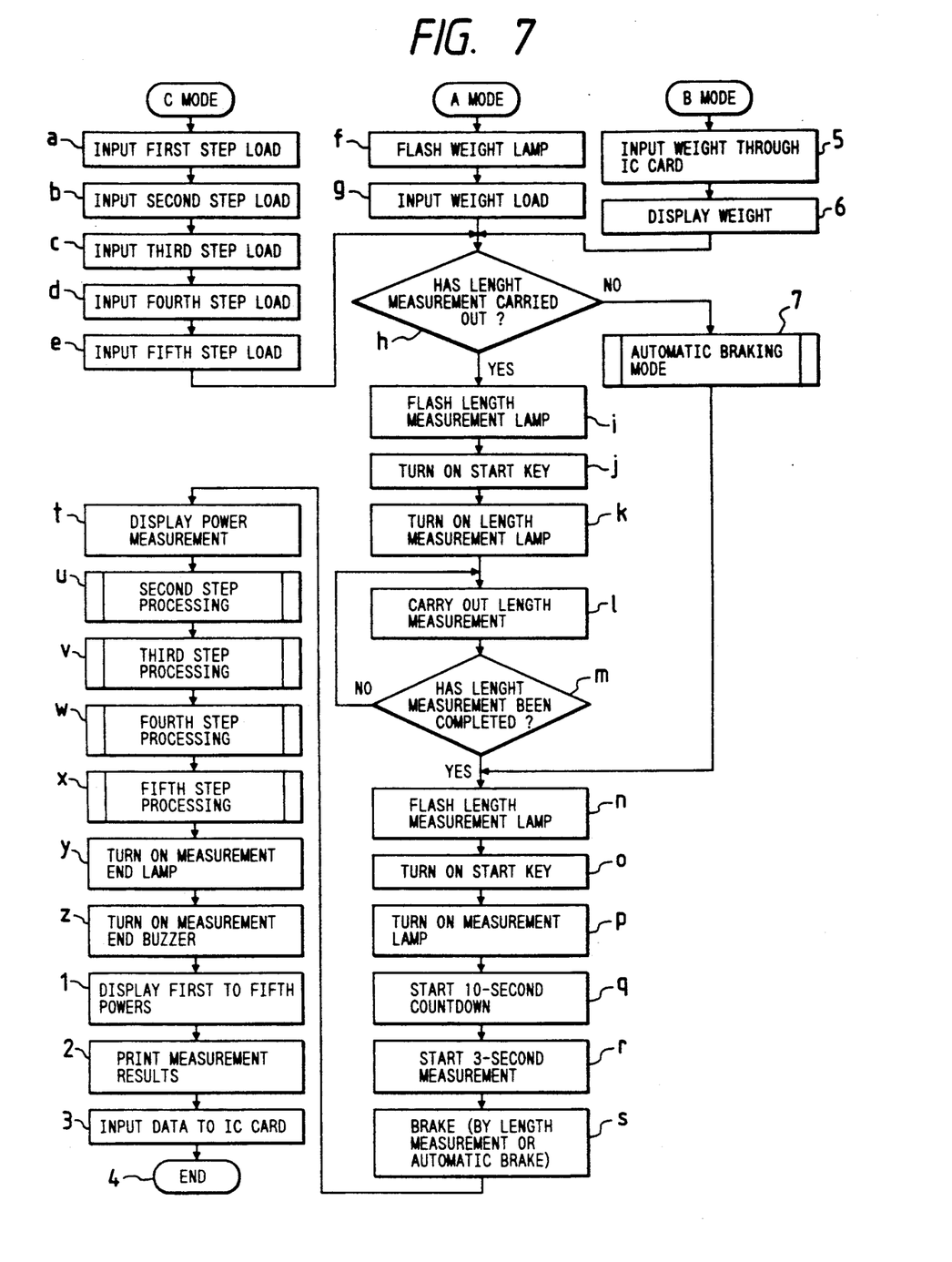
FIG. 7 is a flow chart of a sequence of measurement.

The following is a description of the measuring procedure.

(1) The subject M is seated in the seat 5 and sets the seat 5 by sliding forward and backward while seated such that he or she can kick the foot plate 7e under optimal conditions for measurement. In adjusting the seat 5, the foot plate 7e is fixed by the brake and a resistance from the foot plate 7e is utilized for forward-/backward adjustment.

(2) The subject M then puts his feet on the foot receiving member 7d of the foot plate 7e, thereby fixing his feet on the foot plate 7e by tightening foot belts provided on the foot receiving member 7d. Further, the subject wears a seat belt, provided at the seat 5, around his waist to stably hold the lower half of his body and to secure his position for measurement.

(3) The subject M then operates the mode selector switch 8h positioned close to the display section 9 so as to select a measurement mode as, for example, mode A (the mode in which the subject M enters his weight through the keys to activate a measurement), mode B (the mode in which an IC card is inserted into the IC card reader/writer 12 to activate a measurement in accordance with data recorded in the IC card), and mode C (the mode in which the subject M enters load data corresponding to his physical strength to activate a measurement).

The mode selection is displayed by the LED display unit 9a arranged in the display section 9. When the subject M selects mode A, an LED indicating the input of a weight at the display section 9 is lit. Upon confirmation that the LED is lit, the subject M then operates the keys to enter his or her weight. The entered value is presented to the subject M by means of an LED display unit 9a.

(4) The subject M then presses a length measurement key. Upon pressing this key, the length measurement LED display unit 9a begins to flash, thus informing the subject M that the length measurement key has been operated. In accordance therewith, the subject M operates the start key to allow the subject to kick the foot plate 7e twice, and the length of his or her legs are measured at the time they are extended. In accordance with this length measurement, the microcomputer 8i stores the timing for activating the powder brake 4i4. Accordingly, when the length measurement has been completed, the state of the length measurement LED display unit 9a is changed from flashing to normal lighting, thus informing the subject M that the length measurement has been completed.

The above operation of length measurement is omitted when an automatic brake mode is selected. An automatic brake detects a peak value of $V_{max}$ on a realtime basis and performs a braking function. Since braking is applied to the foot plate after a peak value has been detected, a delay is produced unlike the case in which braking occurs after measurement. Thus, it may be used as a simple system.

(5) Upon completion of the length measurement, the measurement LED display unit 9a flashes, informing the subject M that the system is ready to start measurement. Upon confirming this, the subject M starts the process for measurement of an instantaneous power generated by a leg extending force by pressing the start key. Upon pressing the start key, the measurement LED display unit 9a (which was previously flashing while allowing a measurement to be started) changes to normal lighting, thus informing the subject M that measurement has begun.

If an external display unit is used, the above state can be displayed on the external display unit, simultaneously, by causing the microcomputer 8i to send a predetermined signal thereto. When an external computer or the like is connected, the above state is recorded in the external computer by similarly causing the microcomputer 8i to send a predetermined measurement sequence code thereto.

(6) Upon lighting the measurement LED display unit 9a, the microcomputer 8i signals a timer to begin counting down from 10 seconds until measurement begins. Upon completion of the 10-second countdown, the subject M starts a first-step 3-second instantaneous power measurement. The foot plate 7e kicking timing is signaled by, e.g., the buzzer 9b, and the subject M kicks the foot plate 7e upon buzzing.

When the first step measurement has been ended, it is displayed by the LED display unit 9a and, simultaneously therewith, the power measured in the first step is displayed on the display section 9.

After kicking, the subject M rests for 20 seconds, during which time the foot plate 7e is returned to its original position. The powder brake 4i4 intervenes so as to put the foot plate 7e into a stationary state. (The subject M may then relax as a result of this braking, with his feet rested on the foot plate 7e.)

(7) Twenty seconds after the first step, the measurement LED display unit 9a similarly flashes to indicate to the subject M that the system is ready to make a second step measurement (the same applies similarly to third step, fourth step, and fifth step measurements).

Upon confirming this, the entire process begins again as detailed above.

The measurement results in the first to fifth steps are calculated by the microcomputer 8i on a step basis; i.e., the work corresponding to the equivalent energy of inertia absorbed by the rotary drive system consisting of the powder brake 4i4, the intermediate shaft mechanism 4g, and the rotating shaft 4b of the rope drum 4c, as well as the work corresponding to the kinetic energy obtained by the foot plate 7e are both added to the work done to the powder brake 4i4 to obtain the maximum speed $V_{max}$ of the foot plate 7e and its output time $T_{max}$. And from the maximum speed $V_{max}$ of the foot plate 7e and its output time $T_{max}$, the average power produced by the subject M extending his legs is thus obtained.

(8) Thus, upon completion of the measurements by the first to fifth steps, the end LED display unit 9a is lit to inform the subject M that the measurements have been completed. Simultaneously therewith, the measurement end is confirmed by the buzzer and the measurement results are displayed on the display section 9.

The measurement results are printed by the printer 13 and recorded into the IC card inserted into the IC card reader/writer to complete all of the measurement steps.

As described in the foregoing detailed description, the present invention uses a powder brake as a constant-torque low-inertia load mechanism and thereby measures an instantaneous power generated by an extremely short-time full-power kicking against the foot plate, implementing a kick-based natural physical exercise. As a result, the leg extending force of a subject can be measured easily, with less physical burden imposed on the subject and with an extremely high degree of accuracy. The full-power kicking provides various advantages including measurement of an instantaneous power of a dynamic, nonrepetitive multi-articular movement as, for example, a vertical jump.

What is claimed is:

1. A leg extension apparatus with a pivotal foot section for measuring an instantaneous power generated by a leg extending force, said apparatus comprising:
   a base frame comprising two long members in parallel with each other;
   a vertical plate standing at a front end of said base frame;
   a box disposed in a rear end of said base frame;
   drive means installed inside said box for maintaining a constant load opposing the leg extension;
   a seat, disposed above said drive unit and on an upper surface of said box, for seating a subject;
   a guide section extending in a direction parallel to said base frame between an upper front surface of said box and said vertical plate, with the upper front surface of said box serving as a base end thereof;
   a pivotal foot section slidably movable along said guide section with the leg extension of a subject so that said foot section is caused to pivot in accordance with a position of said foot section along said guide section;
   means for connecting said foot section with said drive means;
   a measuring unit associated with said drive means for measuring sliding conditions of said foot section;
   a display section for displaying various data relating to the leg extension of the subject corresponding to the sliding conditions measured by said measuring unit;
   an input section associated with said measuring unit and said display section for receiving predetermined input data relating to the leg extension of the subject; and
   processor means operably connected to the measuring unit for receiving the measured sliding conditions for calculating the power generated by the leg extending force.

2. An apparatus according to claim 1, wherein said display provides a visual indication of the data relating to the leg extension of the subject.

3. An apparatus according to claim 1, wherein said display provides an aural indication of the data relating to the leg extension of the subject.

4. An apparatus according to claim 1, wherein said two long members have a predetermined distance therebetween, said apparatus further comprising vertically adjustable casters at the rear ends of said long members, and four fixed adjusters, two of said adjusters being provided at each side near a lower front surface of said box and the other two of said adjusters being provided at each side under the vertical plate standing at the front end of said base frame, the four adjusters serving to horizontally hold and stably fix said base frame.

5. An apparatus according to claim 1, wherein said drive means includes:
   a rope;
   a rotating shaft;
   a rope drum around which said rope is wound, said rope drum being mounted on said rotating shaft;
   brackets standing upright at both sides of and toward a front end of said box for supporting said rotating shaft;
   a return spring juxtaposed with said rope drum;
   a first sprocket disposed at one side of said rope drum;
   a first chain wound around said first sprocket;
   an intermediate shaft mechanism rotated unidirectionally through said first chain;
   a second chain wound around said intermediate shaft mechanism; and
   a powder brake mechanism rotated unidirectionally through said second chain.

6. An apparatus according to claim 1, wherein said seat is disposed on the upper surface of said box, said apparatus further comprising horizontally sliding parallel adjust guide shafts, and shaft receiving members protruding from the upper surface of said box, said adjust guide shafts being inserted into said shaft receiving members so that said seat is adjustable, said adjust guide shafts being arranged at both sides of and under a lower surface of said seat.

7. An apparatus according to claim 1, wherein said guide section includes:
   right and left upper guide shafts, each extending horizontally between the upper front surface of said box and said vertical plate; and
   a lower guide shaft running along said upper guide shafts, midway therebetween, and inclined so as to lower a front end thereof, said front end of said lower guide shaft being on a side of said vertical plate.

8. An apparatus according to claim 7, wherein said foot section includes:
   a slider sliding horizontally by inserting said upper guide shafts into right and left insertion holes thereof;
   a bracket provided upright at a front end of the slider;

a foot plate whose back surface is rotatably hinged by said bracket;

a seal boss mounted for oscillatory movement and containing an insertion hole;

a support member extending downward through an opening formed around the center of said slider, said support member being attached to said seal boss by screws through a fork portion thereof; and a foot receiving member on an upper surface of said foot plate on which to place both feet of the subject, said foot section being arranged so that the angle of said foot receiving member of said foot plate is adjustable to a value in accordance with the amount of leg extension of the subject, the angle adjustment being implemented by sliding said foot plate along said lower guide shaft while inserting said lower guide shaft into an insertion hole of said seal boss, said foot plate being slidably mounted on said lower guide shaft through said support.

9. An apparatus according to claim 5, wherein said measuring unit includes:

a drum shaft encoder secured to said rotating shaft of said rope drum;

a forward and backward rotational pulse detection counter of said rope drum, said forward and backward rotational pulse detection counter having a first photosensor for detecting the number of revolutions of said drum shaft encoder, said forward and backward rotational pulse detection counter outputting first pulse signals accordingly;

a rotating shaft of said powder brake mechanism;

a load shaft encoder secured to said rotating shaft of said powder brake mechanism;

a load shaft rotational pulse detection counter for detecting rotation of said powder brake mechanism, said load shaft rotational pulse detection counter having a second photosensor for detecting rotation of said load shaft encoder, said load shaft rotational pulse detection counter outputting second pulse signals accordingly;

a load current adjuster for adjusting current of said powder brake mechanism;

a mode selector switch for selecting a mode signal;

an input section for inputting a data signal; and a processor for calculating a leg extending power in response to at least said first and second pulse signals, said mode signal and said data signal.

10. An apparatus according to claim 1, wherein said measuring unit includes:

an external high level computer;

an IC card reader and writer and a printer for recording measurement results, output data of said IC card reader and writer and said printer being transmitted to and managed by said external high level computer.

11. An apparatus according to claim 5, wherein the forward movement of said foot plate is stopped by activating said powder brake mechanism at a time when said foot plate has reached a maximum extension point, as determined by utilizing the measured length of the legs of the subject, so as to thereby prevent inertial impact.

12. An apparatus for measuring an instantaneous power generated by a leg extending force, said apparatus comprising:

a base frame comprising two long members in parallel with each other;

a vertical plate standing at a front end of said base frame;

a box disposed in a rear end of said base frame;

a drive unit installed inside said box;

a seat, disposed above said drive unit and on an upper surface of said box, for seating a subject;

a guide section extending in a direction parallel to said base frame between an upper front surface of said box and said vertical plate, with the upper front surface of said box serving as a base end thereof;

a foot section disposed for slidable movement along said guide section so as to provide a variable sliding angle;

a measuring unit for measuring sliding conditions of said foot section;

a display section for displaying various data relating to the leg extension of the subject corresponding to said sliding conditions; and an input section for receiving predetermined input data, and wherein said guide section comprises:

right and left upper guide shafts, each extending horizontally between the upper front surface of said box and said vertical plate; and a lower guide shaft running along said upper guide shafts, midway therebetween, and inclined so as to lower a front end thereof, said front end of said lower guide shaft being attached to said vertical plate, and wherein the foot section comprises:

a slider sliding horizontally by inserting said upper guide shafts into right and left insertion holes thereof;

a bracket provided upright at a front end of the slider;

a foot plate whose back surface is rotatably hinged by said bracket;

a seal boss mounted for oscillator movement and containing an insertion hole;

a support member extending downward through an opening formed around the center of said slider, said support member being attached to said seal boss by screws through a fork portion thereof;

a foot receiving member on an upper surface of said foot plate on which to plate both feet of the subject, said foot section being arranged so that the angle of said foot receiving member of said foot plate is adjustable to a value in accordance with the amount of leg extension of the subject, the angle adjustment being implemented by sliding said foot plate along said lower guide shaft while inserting said lower guide shaft into an insertion hole of said seal boss, said foot plate being slidably mounted on said lower guide shaft through said support; and processor means operably connected to the measuring unit for receiving the measured sliding conditions for calculating the power generated by the leg extending force.

13. An apparatus for measuring an instantaneous power generated by a leg extending force, said apparatus comprising:

a base frame comprising two long members in parallel with each other;

a vertical plate standing at a front end of said base frame;

a box disposed in a rear end of said base frame;

a drive unit installed inside said box;

a seat, disposed above said drive unit and on an upper surface of said box, for seating a subject;

a guide section extending in a direction parallel to said base frame between an upper front surface of said box and said vertical plate, with the upper front surface of said box serving as a base end thereof;

a foot section disposed for slidable movement along said guide section so as to provide a variable sliding angle;

a measuring unit for measuring sliding conditions of said foot section;

a display section for displaying various data relating to the leg extension of the subject corresponding to said sliding conditions; and an input section for receiving predetermined input data, and wherein said drive unit comprises:

a rope;

a rotating shaft;

a rope drum around which said rope is wound, said rope drum being mounted on said rotating shaft;

brackets standing upright at both sides of and toward a front end of said box for supporting said rotating shaft;

a return spring juxtaposed with said rope drum;

a first sprocket disposed at one side of said rope drum;

a first chain wound around said first sprocket;

an intermediate shaft mechanism rotated unidirectionally through said first chain;

a second chain wound around said intermediate shaft mechanism; and a powder brake mechanism rotated unidirectionally through said second chain, and wherein said measuring unit includes:

a drum shaft encoder secured to said rotating shaft of said rope drum;

a forward and backward rotational pulse detection counter of said rope drum, said forward and backward rotational pulse detection counter having a first photosensor for detecting the number of revolutions of said drum shaft encoder, said forward and backward rotational pulse detection counter outputting first pulse signals accordingly;

a rotating shaft of said powder brake mechanism;

a load shaft encoder secured to said rotating shaft of said powder brake mechanism;

a load shaft rotational pulse detection counter for detecting rotation of said powder brake mechanism, said load shaft rotational pulse detection counter having a second photosensor for detecting rotation of said load shaft encoder, said load shaft rotational pulse detection counter outputting second pulse signals accordingly;

a load current adjuster for adjusting current of said powder brake mechanism;

a mode selector switch for selecting a mode signal;

an input section for inputting a data signal; and a processor for calculating a leg extending power in response to at least said first and second pulse signals, said mode signal and said data signal.

* * * * *